(12) United States Patent
Stewart et al.

(10) Patent No.: US 8,678,002 B2
(45) Date of Patent: Mar. 25, 2014

(54) DEVICES AND METHODS FOR DECREASING HUMAN PATHOGEN TRANSMISSION

(75) Inventors: Neal G. Stewart, Hong Kong (CN); Lok Yuen Lo, Hong Kong (CN); Francis Chi Nan Lau, Belmont, CA (US); Dacey J. Ryan, Hong Kong (CN); Reid W. von Borstel, Potomac, MD (US)

(73) Assignee: Filligent Limited, Sheung Wan (HK)

( * ) Notice: Subject to any disclaimer, the term of this patent is extended or adjusted under 35 U.S.C. 154(b) by 526 days.

(21) Appl. No.: 12/666,291

(22) PCT Filed: Jun. 25, 2008

(86) PCT No.: PCT/US2008/068225
§ 371 (c)(1),
(2), (4) Date: Dec. 22, 2009

(87) PCT Pub. No.: WO2009/003057
PCT Pub. Date: Dec. 31, 2008

(65) Prior Publication Data
US 2010/0330140 A1 Dec. 30, 2010

Related U.S. Application Data

(60) Provisional application No. 60/946,267, filed on Jun. 26, 2007, provisional application No. 61/057,742, filed on May 30, 2008.

(51) Int. Cl.
*A62B 18/08* (2006.01)
*A62B 7/10* (2006.01)
*A01N 25/34* (2006.01)
*A61K 33/34* (2006.01)

(52) U.S. Cl.
USPC ................ 128/206.12; 128/206.19; 424/411; 424/637

(58) Field of Classification Search
USPC ............. 128/206.12, 206.13, 206.19, 206.21; 424/411, 618, 637, 641
See application file for complete search history.

(56) References Cited

U.S. PATENT DOCUMENTS 588,274 A * 8/1897 Harris ........................... 280/261
4,536,440 A 8/1985 Berg
(Continued)

FOREIGN PATENT DOCUMENTS

WO 9932707 A1 7/1999
WO 2004110401 A2 12/2004

OTHER PUBLICATIONS

Shears, K. H., "After N-9, What Next? Several Potential Microbicides Are Poised to Be Tested for Effectiveness in Humans," Network, Summer, 2003, 2 pages.
(Continued)

*Primary Examiner* — Quynh-Nhu H Vu
(74) *Attorney, Agent, or Firm* — Trojan Law Offices

(57) ABSTRACT

A facial mask for use in decreasing the transmission of one or more than one human pathogen to and from a human wearer of the facial mask, the facial mask comprising a facepiece; where the facepiece comprises three or more than three layers; where one or more than one of the three or more than three layers comprises a fabric comprising one or more than one binding substance comprising one or more than one human pathogen binding group for chemically attaching the human pathogen to the binding substance; where the fabric further comprises one or more than one type of multivalent metallic ion or metallic salt; and where one or more than one of the three or more than three layers comprises a heat-moldable fabric.

44 Claims, 5 Drawing Sheets

(56) References Cited

U.S. PATENT DOCUMENTS

| | | | |
|---|---|---|---|
| 4,643,182 A * | 2/1987 | Klein | 128/201.25 |
| 4,841,029 A * | 6/1989 | Kato et al. | 534/634 |
| 4,869,826 A * | 9/1989 | Wang et al. | 210/679 |
| 5,012,505 A * | 4/1991 | Zupancic et al. | 378/130 |
| 5,094,236 A * | 3/1992 | Tayebi | 128/206.12 |
| 5,447,589 A * | 9/1995 | DeLangis | 156/88 |
| 5,447,859 A * | 9/1995 | Prussak | 435/239 |
| 5,763,078 A * | 6/1998 | Braun et al. | 428/175 |
| 5,888,274 A | 3/1999 | Frederick | |
| 6,120,784 A | 9/2000 | Snyder, Jr. | |
| 6,681,765 B2 * | 1/2004 | Wen | 128/201.25 |
| 7,008,465 B2 * | 3/2006 | Graham et al. | 95/78 |
| 7,288,264 B1 | 10/2007 | Sawan et al. | |
| 2002/0127282 A1 * | 9/2002 | Antelman | 424/618 |
| 2003/0111075 A1 | 6/2003 | Wen | |
| 2004/0081761 A1 * | 4/2004 | Tyvoll | 427/304 |
| 2004/0173227 A1 | 9/2004 | Von Borstel | |
| 2006/0130841 A1 * | 6/2006 | Spence et al. | 128/206.19 |
| 2007/0295334 A1 * | 12/2007 | Nonomura | 128/206.13 |
| 2008/0142445 A1 * | 6/2008 | Haj-Ahmad | 210/660 |
| 2008/0251081 A1 * | 10/2008 | Claussen et al. | 128/205.27 |
| 2009/0263371 A1 * | 10/2009 | Riske et al. | 424/94.61 |

OTHER PUBLICATIONS

International Search Report and Written Opinion issued in related International Patent Application No. PCT/US2009/48706 dated Sep. 10, 2009, 12 pages.

Hungarian Intellectual Property Office, Written Opinion, Feb. 14, 2011.

Printout of website at http://en.wikipedia.org/wiki/Sialic_acid.

David T.W. Chun, et al., Using the Reactive Dye Method to Attach Antibacterial Compounds to Cotton, 2007 Beltwide Cotton Conferences, New Orleans, Louisiana, Jan. 9-12, 2007, p. 1242.

International Search Report and Written Opinion issued in parent International Patent Application No. PCT/US08/68225 dated Oct. 3, 2008.

* cited by examiner

DEVICES AND METHODS FOR DECREASING HUMAN PATHOGEN TRANSMISSION

CROSS-REFERENCE TO RELATED APPLICATIONS

The present Application is a 371 of International Patent Application No. PCT/US2008/068225 filed Jun. 25, 2008 and titled "Devices and Methods for Decreasing Human Pathogen Transmission," which claims priority from U.S. Provisional Patent Application No. 61/057,742 filed May 30, 2008 and titled "Protective Fabrics and Method for Making Protective Fabrics"; and also claims priority from U.S. Provisional Patent Application No. 60/946,267, filed Jun. 26, 2007 and titled "Protective Fabrics and Method of Making Protective Fabrics," the contents of which are incorporated in this disclosure by reference in their entirety.

BACKGROUND

There are a variety of infectious human diseases, such as human respiratory tract infections, that are caused by human pathogens such as bacteria, fungi and viruses. For example, viral causes of infectious human diseases (and their associated diseases) include: Influenza A virus (influenza); Influenza B-C virus (coryza; 'common cold'); Human adenovirus A-C (various respiratory tract infections; pneumonia); Human Para-influenza virus (coryza; 'common cold;' croup); Mumps virus (epidemic parotitis); Rubeola virus (measles); Rubella virus (German measles); Human respiratory syncytial virus (RSV) (coryza; 'common cold'); Human coronavirus (SARS virus) (SARS); Human rhinovirus A-B (coryza; 'common cold'); parvovirus B19 (fifth disease); variola virus (smallpox); varicella-zoster virus (herpes virus) (chickenpox); Human enterovirus (coryza; 'common cold'); Bordetella pertussis (whooping cough); Neisseria meningitidis (meningitis); Corynebacterium diphtheriae (diphtheria); Mycoplasma pneumoniae (pneumonia); Mycobacterium tuberculosis (tuberculosis); Streptococcus pyogenes/pneumoniae (strep throat, meningitis, pneumonia); and Haemophilus influenzae Type B (epiglottis, meningitis, pneumonia).

Many of the human viral respiratory tract infections result in significant morbidity and mortality. For example, seasonal epidemics of influenza viruses worldwide infect an estimated 3 million to 5 million people, and kill between 250,000 to 500,000 people each year. In addition, cyclical influenza virus pandemics occur, such as the influenza outbreak in 1918 which killed approximately 20 million people worldwide.

The mode of transmission of one or more than one human pathogen that causes human respiratory tract infections was believed to be primarily by direct skin to skin contact; however, it has been shown that many human pathogens are also spread by airborne transmission of pathogen-laden droplets expelled from the respiratory tract of infected individuals by coughing or sneezing, or by simple exhalation.

Vaccines are available against some human pathogens that cause human respiratory tract infections, and medications have been developed that are effective against some of the human pathogens. Vaccines, however, do not provide immediate protection but require time sufficient for development of an antibody response before they can reduce the transmission of the human pathogen. Additionally, effective medications that can reduce transmission are not available for most of the human viral pathogens and for some of the human non-viral pathogens.

Therefore, there is a need for a new method for preventing airborne transmission of one or more than one human pathogen that causes human respiratory tract infections, among other diseases.

SUMMARY

According to one embodiment of the present invention, there is provided a facial mask for use in decreasing the transmission of one or more than one human pathogen to and from a human wearer of the facial mask. In one embodiment, the facial mask comprises a) a facepiece comprising a front side, a back side and a perimeter around the front side and back side, and the facepiece is configured to cover the mouth and nose of the wearer of the facial mask; and b) one or more than one extension attached to the facepiece for securing the facial mask to the head of the wearer; where the facepiece comprises three or more than three layers; where one or more than one of the three or more than three layers comprises a fabric comprising one or more than one binding substance; where the one or more than one binding substance comprises one or more than one human pathogen binding group for chemically attaching the human pathogen to the binding substance; where the fabric further comprises one or more than one type of multivalent metallic ion or metallic salt; and where one or more than one of the three or more than three layers comprises a heat-moldable fabric. In one embodiment, the facepiece comprises a substantially semi-circular lower half, and comprises an upper half with cheek extensions laterally, and a central nose bridge extension between the two cheek extensions configured to extend above the nostrils of the wearer, and onto the bridge of the nose of the wearer.

According to another embodiment of the present invention, there is provided a facial mask for use in decreasing the transmission of one or more than one human pathogen to and from a human wearer of the facial mask. In one embodiment, the facial mask comprises a) a facepiece comprising a front side, a back side and a perimeter around the front side and back side, and the facepiece configured to cover the mouth and nose of the wearer of the facial mask; and b) one or more than one extension attached to the facepiece for securing the facial mask to the head of the wearer; where the facepiece comprises a fabric comprising one or more than one binding substance comprising one or more than one human pathogen binding group for chemically attaching the human pathogen to the binding substance. In one embodiment, the one or more than one human pathogen is selected from the group consisting of bacteria, fungi and viruses that cause human diseases. In one embodiment, the human pathogen is one or more than one virus that causes human respiratory tract infections. In one embodiment, the one or more than one human pathogen is selected from the group consisting of adeno-associated virus (AAV), herpes simplex virus (HSV), human papillomavirus (HPV), influenza viruses, rabies virus and respiratory syncytial virus (RSV). In one embodiment, the fabric further comprises one or more than one type of multivalent metallic ion. In one embodiment, the one or more than one type of multivalent metallic ion is selected from the group consisting of multivalent copper, multivalent silver and multivalent zinc. In one embodiment, the fabric further comprises one or more than one metallic salt selected from the group consisting of copper acetate, copper oxide, copper sulfate and zinc acetate. In one embodiment, the facepiece comprises a plurality of layers; and one or more than one of the plurality of layers comprises the fabric comprising the one or more than one binding substance. In one embodiment, one or more than one of the plurality of layers comprises a heat-moldable fabric. In one embodiment, one or more than one of the plurality of layers comprises a fabric selected from the group consisting of polypropylene, polyester or cellulose acetate nonwoven fabric. In one embodiment, one or more than one of the plurality of layers comprises polypropylene webbing. In one embodiment, the plurality of layers comprises three layers. In one embodiment, the plurality of layers comprises four layers. In one embodiment, the perimeter of the facepiece comprises a semi-circular lower half, and a semi-circular upper half with a central nose bridge extension configured to extend above the nostrils of the wearer, and onto the bridge of the nose of the wearer. In one embodiment, the facepiece comprises a substantially semi-circular lower half, and comprises an upper half with cheek extensions laterally, and a central nose bridge extension between the two cheek extensions configured to extend above the nostrils of the wearer, and onto the bridge of the nose of the wearer. In one embodiment, the facepiece is convex toward the front side in order to more closely approximate facial curves of the wearer of the facial mask. In one embodiment, the perimeter of the facepiece comprises a top edge, a bottom edge, two lateral edges connecting the top edge with the bottom edge; and the facepiece further comprises a plurality of pleats extending from one lateral edge to the other lateral edge, the pleats allowing expansion of the facepiece centrally thereby forming a convex shape toward the front side of the facepiece when expanded, in order to more closely approximate the facial curves of a wearer of the facial mask. In one embodiment, the one or more than one extension is selected from the group consisting of a strap, an ear loop and an adhesive strip.

According to another embodiment of the present invention, there is provided a facial mask for use in decreasing the transmission of one or more than one human pathogen to and from a human wearer of the facial mask. The facial mask comprises a) a facepiece comprising a front side, a back side and a perimeter, and configured to cover the mouth and nose of the wearer of the facial mask; b) a removable filter comprising a fabric comprising one or more than one binding substance that binds the one or more than one human pathogen; and c) a mechanism attached to the facepiece for holding the filter.

According to another embodiment of the present invention, there is provided a gas mask for use in decreasing the transmission of one or more than one human pathogen to and from a human wearer of the gas mask. The gas mask comprises a) a removable filter comprising a fabric comprising one or more than one binding substance that binds the one or more than one human pathogen; and b) a mechanism attached for holding the filter. In one embodiment, the filter comprises a material comprising a plurality of layers, where one or more than one of the plurality of layers comprises the fabric comprising one or more than one binding substance that binds the one or more than one human pathogen.

According to another embodiment of the present invention, there is provided a device for use in decreasing the transmission of one or more than one human pathogen. The device comprises a fabric comprising one or more than one binding substance comprising one or more than one human pathogen binding group for chemically attaching the human pathogen to the binding substance; and the device is selected from the group consisting of an air filter, an article of clothing, bed clothes, a cosmetic pad, a covering for a facial mask or breathing apparatus, a diaper, a dry sanitizing patch, a sanitary pad, a toilet cover, upholstery, a wipe, and a window covering. In one embodiment, the device further comprises a plurality of layers; and one or more than one of the plurality of layers comprises the fabric comprising the one or more than one binding substance. In one embodiment, one or more than one of the plurality of layers comprises a heat-moldable fabric. In one embodiment, one or more than one of the plurality of layers comprises a fabric selected from the group consisting of polypropylene, polyester or cellulose acetate nonwoven fabric. In one embodiment, one or more than one of the plurality of layers comprises polypropylene webbing. In one embodiment, the plurality of layers comprises three layers. In one embodiment, the plurality of layers comprises four layers.

According to another embodiment of the present invention, there is provided a method for making a facial mask. In one embodiment, the method comprises a) providing a fabric comprising one or more than one binding substance comprising one or more than one human pathogen binding group for chemically attaching the human pathogen to the binding substance; and b) incorporating the fabric into the facial mask. In one embodiment, the facial mask comprises a removable filter comprising the fabric; and the method comprises incorporating the removable filter into the facial mask. In one embodiment, the method further comprises enclosing or surrounding the fabric comprising the binding substance between sheets of heat-moldable fabric. In one embodiment, the method further comprises heating or welding the sheets of heat-moldable fabric together. In one embodiment, the method further comprises adding one or more than one additional substance, other than the binding substance, that decreases the pathogenic capacity of one or more than one human pathogen. In one embodiment, the one or more than one additional substance is a multivalent metallic ion or metallic salt.

According to another embodiment of the present invention, there is provided a method of decreasing the transmission of one or more than one human pathogen. The method comprises a) providing a facial mask according to the present invention; and b) wearing the facial mask.

According to another embodiment of the present invention, there is provided a material for use in decreasing the transmission of one or more than one human pathogen. The material comprises a plurality of layers; where one or more than one of the plurality of layers comprises the fabric comprising the one or more than one binding substance. In one embodiment, one or more than one of the plurality of layers comprises a heat-moldable fabric. In one embodiment, one or more than one of the plurality of layers comprises a fabric selected from the group consisting of polypropylene, polyester or cellulose acetate nonwoven fabric. In one embodiment, one or more than one of the plurality of layers comprises polypropylene webbing. In one embodiment, the plurality of layers comprises three layers. In one embodiment, the plurality of layers comprises four layers.

FIGURES

These and other features, aspects and advantages of the present invention will become better understood with regard to the following description, appended claims, and accompanying figures where:

FIG. 1 is a partial frontal perspective view of a fabric according to the present invention;

FIG. 2 is a partial, cutaway, frontal perspective view of a material according to the present invention, comprising the fabric shown in FIG. 1;

FIG. 3 is a front perspective view of a facial mask according to one embodiment of the present invention;

FIG. 4 is a back perspective view of the facial mask shown in FIG. 3;

FIG. 5 is a front perspective view of a facial mask according to another embodiment of the present invention;

DESCRIPTION

Figure 1:
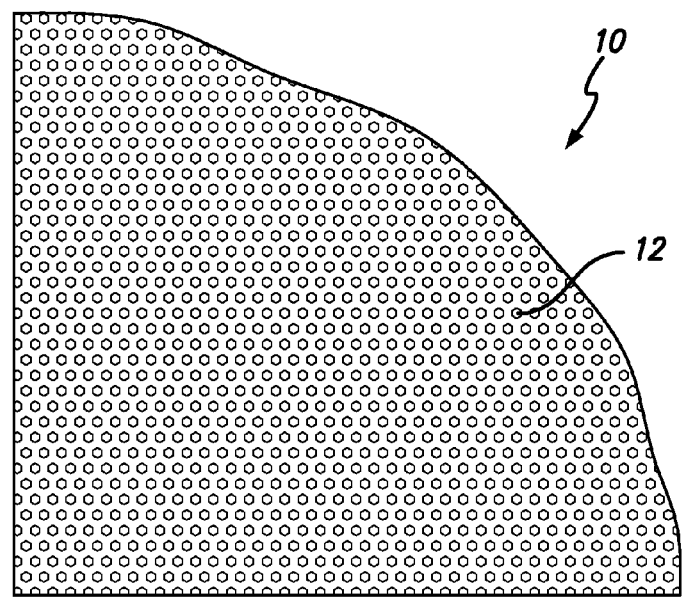

According to the present invention, there is provided a fabric for use in decreasing the transmission of one or more than one human pathogen. According to the present invention, there is provided a material for use in decreasing the transmission of one or more than one human pathogen, where the material comprises a plurality of layers, and where one or more than one of the plurality of layers comprises a fabric according to the present invention. According to another embodiment of the present invention, there is provided a method for making a fabric for use in decreasing the transmission of one or more than one human pathogen. In one embodiment, the method produces a fabric according to the present invention. According to another embodiment of the present invention, there is provided a method for making a material for use in decreasing the transmission of one or more than one human pathogen. In one embodiment, the method produces a material according to the present invention. According to another embodiment of the present invention, there is provided a device for use in decreasing the transmission of one or more than one human pathogen. In one embodiment, the device comprises a fabric according to the present invention. In one embodiment, the device comprises a material according to the present invention. In a preferred embodiment, the device is a facial mask for decreasing the transmission of one or more than one human pathogen to and from a human wearer of the facial mask. According to another embodiment of the present invention, there is provided a method for making a device for use in decreasing the transmission of one or more than one human pathogen. In one embodiment, the method produces a device according to the present invention. According to another embodiment of the present invention, there is provided a method of decreasing the transmission of one or more than one human pathogen. In one embodiment, the method comprises providing a device according to the present invention, such as a facial mask according to the present invention. The fabric, material, device and methods will now be disclosed in greater detail.

As used in this disclosure, except where the context requires otherwise, the term "comprise" and variations of the term, such as "comprising," "comprises" and "comprised" are not intended to exclude other additives, components, integers or steps.

All dimensions specified in this disclosure are by way of example only and are not intended to be limiting. As will be understood by those with skill in the art with reference to this disclosure, the actual dimensions of any device or part of a device disclosed in this disclosure will be determined by its intended use.

As used in this disclosure, "human pathogen" comprises bacteria, fungi and viruses that cause human diseases, including bacteria, fungi and viruses that cause human respiratory tract infections.

As used in this disclosure, "binding substance" means a chemical group that chemically binds a human pathogen, rather than presenting only a physical barrier to spatial passage of the human pathogen. Similarly, "bind," and its related terms such as "binds," "binding" and "binding action," refer to a chemical process, not merely the presentation of only a physical barrier to the spatial passage of the human pathogen.

As used in this disclosure, "cellulosic" means "comprising cellulose."

According to the present invention, there is provided a fabric for use in decreasing the transmission of human pathogens. In one embodiment, the fabric comprises one or more than one binding substance that binds one or more than one type of human pathogen. In a preferred embodiment, the fabric comprises one or more than one binding substance that binds one or more than one type of virus, such as influenza virus, that causes human respiratory tract infections such as influenza. By binding the human pathogen to the fabric, the fabric decreases the transmission of the human pathogen, such as for example by preventing release of virus particles when virus-laden droplets evaporate within the fabric.

The one or more than one binding substance comprises one or more than one human pathogen binding group for chemically attaching the human pathogen to the binding substance, as will be understood by those with skill in the art with reference to this disclosure. In a preferred embodiment, the binding substance further comprises a linker group (such as for example a vinyl sulfone group) for attaching the binding substance to the fabric.

By way of example, in one embodiment, the human pathogen to be bound to the fabric is selected from the group consisting of adeno-associated virus (AAV), herpes simplex virus (HSV), human papillomavirus (HPV), influenza viruses, rabies virus, respiratory syncytial virus (RSV), and the human pathogen binding group is a sialic acid group because these virus particles bind to human cells through a terminal sialic acid group on a surface oligosaccharide of the cell membrane of human cells. Sialic acid groups are, however, relatively expensive to produce in a form suitable for attachment to fibers or fabrics, and therefore, in a preferred embodiment, the binding substance is a substance that mimics the binding action of sialic acid groups on influenza viruses, but that is cost effective as a component for industrial-scale production of fabrics comprising the binding substance according to the present invention.

According to one embodiment of the present invention, the one or more than one binding substance comprises a human pathogen binding group selected from the group consisting of a sulfate group (such as for example, sulfated monosaccharide or sulfated oligosaccharide) and a sulfonate group (such as for example sulfonated monosaccharide or sulfonated oligosaccharide), because both sulfate groups and sulfonate groups mimic the binding action of sialic acid groups on adeno-associated virus (AAV), herpes simplex virus (HSV), human papillomavirus (HPV), influenza viruses, rabies virus, respiratory syncytial virus (RSV), as well as other human pathogens, while sulfate groups and sulfonate groups can be directly linked to free hydroxyl groups and free amino groups on fibers or fabrics in a cost effective manner for industrial-scale production in fabrics according to the present invention. In a preferred embodiment, the fabric is a cellulosic fabric (i.e., comprises cellulose) and the one or more than one binding substance comprises a human pathogen binding group comprising a sulfate group, yielding a fabric comprising a non-hydrogel cellulose sulfate.

According to another embodiment of the present invention, the human pathogen binding group is one or more than one reactive dye comprising one or more than one sulfonate group. In a preferred embodiment, the fabric is a cellulosic fabric (i.e., comprises cellulose) and the binding substance is one or more than one reactive dye comprising a binding substance comprising a sulfonate group, yielding a fabric comprising a cellulose sulfonate.

Reactive dyes are a class of substances used to dye fibers and fabrics, both cellulosic fibers and cellulosic fabrics (such as acetate, cotton and rayon), and non-cellulosic fibers and non-cellulosic fabrics (such as wool and nylon, and fabrics made from polyester or polyolefin). Reactive dyes comprise a reactive linker group, usually either a haloheterocycle or an activated double bond that, when applied to a fiber in a dye bath, forms a covalent chemical bond with an hydroxyl group on the fiber or the fabric. Reactive dyes are classified according to the category of linker group that attaches the dye to the fiber or fabric. In one embodiment, the binding substance is one or more than one reactive dye selected from the group consisting of aminochlorotriazine (Procion® H), aminochlorotriazine-sulfatoethylsulfone (Sumafix Supra), aminofluorotriazine (Cibachron F), aminofluorotriazine-sulfatoethylsulfone (Cibacron C), bis(aminochlorotriazine) (Procion® H-E) bis(aminonicotinotriazine) (Kayacelon React®), chlorodifluoropyrimidine (Drimarine K), dichloroquinoxaline (Levafix® E), dichlorotriazine (Procion MX), sulfatoethylsulfone (vinyl sulfone; Remazol®), sulfatoethylsulfonamide (Remazol® D), trichloropyrimidine (Drimarine X). Reactive Dyes further comprise a chromophore group, providing the specific color for the dye. The chromophore group commonly comprises a multi-ring aromatic group; however, multi-ring aromatic groups tend to decrease water solubility, so reactive dyes usually further comprise one or more sulfonate groups to increase water solubility. The sulfonate groups of reactive dyes can function as the human pathogen binding group of the binding substance of the fabrics of the present invention, while the reactive linker groups of the reactive dyes can function as the linker group of the binding substance.

A given dye frequently has several trade names, but the generic names (Color Index; CI) for dyes comprise the following format: [Category (acidic, basic, direct or reactive); Color; and Number]. According to one embodiment of the present invention, the one or more than one binding substance is a reactive dye selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86, each of which comprises sulfonate groups which function as the human pathogen binding group suitable for binding one or more than one human pathogen according to the present invention, and each of which further comprises a linker group suitable for attaching the binding substance (the dye) to the fabric. In a particularly preferred embodiment, the binding substance is CI Reactive Blue 21 (copper, (29H,31H-phthalocyaninato (2-)-N\29\,N\30\,N\31\,N\32\)-, sulfo((4-((2-sulfooxy)ethyl)sulfonyl)phenyl)amino)sulfonyl derivs] (CAS Reg. No. 73049-92-0), a sulfonated copper phthalocyanine dye with a vinyl sulfone linker group that attaches the dye to fibers and fabrics, including cellulosic fibers and fabrics. The appropriate reaction conditions for attaching reactive dyes, including for attaching CI Reactive Blue 21, to fibers and fabrics are well known to those with skill in the art, and can be found in instructions from the dye manufacturers, as well as in standard textile references, as will be understood by those with skill in the art with reference to this disclosure.

As will be understood by those with skill in the art with reference to this disclosure, the binding substance cannot render the fabric impermeable to gases when the fabric is to be incorporated into the facepiece of a facial mask according to the present invention because such impermeability would render the facial mask non-functional, as will be understood by those with skill in the art with reference to this disclosure. For example, if the human pathogen binding group is a sulfate group, the sulfate group cannot form a cellulose sulfate hydrogel within the fabric because cellulose sulfate hydrogels would block the passage of air through a facial mask rendering the facial mask non-functional and, therefore, the use of the term "cellulose sulfate" and its related terms when referencing the content of a fabric according to the present invention is understood not to comprise a cellulose sulfate hydrogel or any form that is impermeable to gas that would block the passage of air through a facial mask rendering the facial mask non-functional (that is, rendering a wearer unable to breathe adequately through the facial mask). Using a reactive dye as the binding substance in the fabric according to the present invention is particularly advantageous because the amount of reactive dye binding to a fabric is never high enough to cause the sulfonate groups in the reactive dyes to make a hydrogel in the fabric.

As will be understood by those with skill in the art with reference to this disclosure, both cellulose sulfate and cellulose sulfonate have surfactant properties, so that fabrics comprising cellulose sulfate or cellulose sulfonate disrupt virus-laden droplets and exposes the virus particles to the sulfate groups on the cellulose sulfate, and to the sulfonate groups on the cellulose sulfonate, thereby trapping the virus particles within the fabric.

In one embodiment, the fabric of the present invention further comprises one or more than one additional substance, other than the binding substance and the fibers of the fabric, that decreases the pathogenic capacity of one or more than one human pathogen. In a preferred embodiment, the one or more than one additional substance is one or more than one type of multivalent metallic ion, such as for example multivalent copper, multivalent silver or multivalent zinc, all of which are viricidal, bactericidal and fungicidal. In a preferred embodiment, the metallic salt is a divalent metallic salt. In another embodiment, the one or more than one substance is a metallic salt, such as for example copper oxide, zinc acetate, copper acetate, or copper sulfate all of which are bactericidal, viricidal and fungicidal.

As will be understood by those with skill in the art with reference to this disclosure, using a binding substance comprising a sulfate group or a sulfonate group on a fabric comprising cellulose is both relatively inexpensive and suitable for industrial-scale production of facial masks according to the present invention to protect large populations from the transmission of influenza viruses and other human pathogens. Further, the fabric according to the present invention is safe to both people and pets, for example by replacing toxic antimicrobial compounds used in some facial masks, and by binding the virus particles within the fabric so that the virus particles do not leach out of the fabric after the virus particles contact the fabric. Further advantageously, the fabric of the present invention does not require illumination and singlet oxygen generation for decreasing the transmission of one or more than one human pathogen, as with some fabrics designed to decrease transmission of one or more than one human pathogen.

In one embodiment, the fabric is woven, such as for example woven rayon. In another embodiment, the fabric is non-woven, such as for example non-woven rayon.

Figure 2:
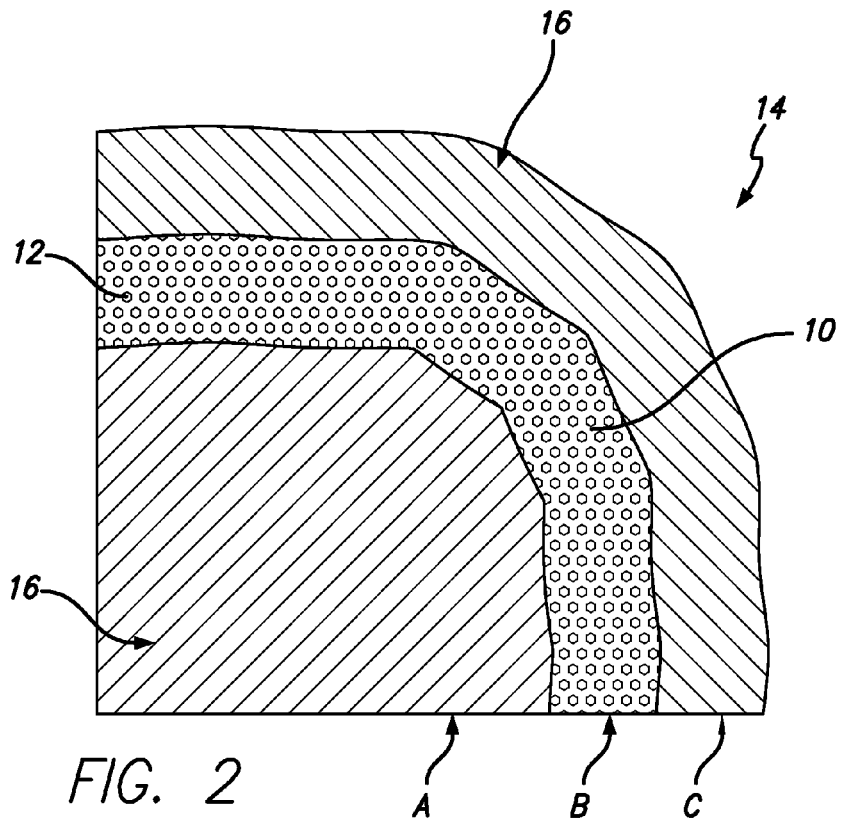

According to the present invention, there is provided a material for use in decreasing the transmission of one or more than one human pathogen, where the material comprises a plurality of layers, and where one or more than one of the plurality of layers comprises a fabric according to the present invention. Referring now to FIG. 1 and FIG. 2, there is shown, respectively, a partial frontal perspective view of a fabric according to the present invention (FIG. 1); and a partial, cutaway, frontal perspective view of a material according to the present invention, comprising the fabric shown in FIG. 1 (FIG. 2). As can be seen, the fabric 10 according to the present invention comprises binding substances 12. Further, the material 14, comprises a plurality of layers, designated here A, B and C. The material 14 can comprise two layers, three layers (as shown), four layers or more than four layers, as will be understood by those with skill in the art with reference to this disclosure. In a particularly preferred embodiment, the plurality of layers is three layers (as shown). In another particularly preferred embodiment, the plurality of layers is four layers.

At least one of the layers of the material 14 comprises a fabric 10 (here shown as layer B) according to the present invention. In one embodiment, one or more than one of the layers of the material 14 is a heat-moldable fabric 16, such as a heat-moldable fabric selected from the group consisting of polypropylene, polyester and non-woven cellulose acetate fabric. Such heat-moldable fabrics permit shaping of facial masks with heat or ultrasonic welding according to the present invention. In one embodiment, the heat-moldable fabric comprises polypropylene webbing which traps airborne particles, but is relatively water repellent so that virus-laden droplets are normally not disrupted even if the virus-laden droplets are trapped within the webbing.

According to another embodiment of the present invention, there is provided a method for making a fabric for use in decreasing the transmission of one or more than one human pathogen, such as for example viruses that cause human respiratory tract infections. In one embodiment, the method produces a fabric according to the present invention. The method will now be disclosed by way of example only primarily with respect to making a fabric comprising cellulose (in this example, rayon) with binding substances comprising sulfate groups as the human pathogen binding group, though other methods can be used to produce the same fabric, and corresponding fabrics with other binding substances (such as sulfonate groups) according to the present invention, as will be understood by those with skill in the art with reference to this disclosure.

In one embodiment, the method comprises, first, providing fibers suitable for use in a fabric for decreasing the transmission of one or more than one human pathogen. In one embodiment, the fabric comprises cellulose. In a preferred embodiment, the fabric comprises rayon (a form of cellulose). The most important source of cellulose fibers for commercial purposes is from wood pulp; however, cellulose fibers obtained directly from wood pulp are too short and coarse to weave into a fabric according to the present invention, and cellulose derived from wood pulp is relatively insoluble in organic solvents and cannot be extruded into fine fibers. By contrast, rayon fibers are produced from naturally occurring cellulose polymers derived from wood pulp and other plants. To form rayon fibers, the cellulose is first derivatized with solubilizing groups (such as for example acetate), formed into spun fibers, and then, the solubilizing groups are removed yielding cellulose fibers that can be woven into fabric, as will be understood by those with skill in the art with reference to this disclosure.

Next, the method comprises adding one or more than one binding substance to the fibers. Adding the binding substance to the fibers can be accomplished using techniques known to those with skill in the art, as will be understood by those with skill in the art with reference to this disclosure. In a preferred embodiment, the binding substance added is a binding substance according to the present invention. By way of example, the method will be disclosed with respect to binding substances comprising a human pathogen binding group that comprises a sulfate group, thereby yielding sulfated cellulose fibers. In this embodiment, adding one or more than one binding substance to the fibers results in sulfation of the cellulose derived fibers in the fabric without disrupting the structure or strength of the fabric. Further, though these steps are disclosed with respect to covalently bonding sulfate groups to cellulosic fibers (such as rayon), equivalent steps can be used for adding sulfate groups to other cellulosic fabrics, blends of cellulose-derived and noncellulose-derived fibers (such as for example fibers made from polyester or polyolefin) and noncellulose-derived fibers that comprise free hydroxyl or amino groups, as will be understood by those with skill in the art with reference to this disclosure.

Cellulose is a linear polymer of glucose units, each of which has three free hydroxyl groups. The degree of sulfation (DS) of cellulose is defined in the art as the average number of sulfate groups per monosaccharide unit. A DS of 3 is the maximum possible, indicating that all available hydroxyl groups are fully sulfated. A degree of sulfation of 1 indicates that an average of one sulfate group per glucose unit is present, and a DS of 0.1, for example, indicates that an average of one hydroxyl group of every ten glucose units is sulfated. An important aspect of the present invention is that the binding of viruses and other human pathogens to a fiber or fabric according to the present invention involves binding of the human pathogen to more than one immobilized sulfate group or sulfonate group on the fiber or fabric, thereby strongly increasing the affinity of the interaction between the binding substance and the human pathogen.

The degree of sulfation is determined by any suitable analytical method that measures sulfate, sulfonate or total sulfur, such as for example by elemental analysis. The sulfur content of cellulose fibers without a binding substance attached or nonpigmented cellulose fibers or fabrics is extremely low or undetectable. According to one embodiment of the present invention, the present method results in a degree of sulfation between 0.02 and 2. In a preferred embodiment of the present invention, the present method results in a degree of sulfation between 0.05 and 0.5. In a particularly preferred embodiment, the present method results in a degree of sulfation of between 0.09 and 0.21. The degree of sulfation for sulfated or sulfonated fibers or fabric can be regulated by adjusting the time, temperature or reagent concentrations in a sulfation or sulfonation reaction, as will be understood by those with skill in the art with reference to this disclosure, to produce fibers with the required degree of sulfation.

As the degree of sulfation increases above 0.2 for a cellulosic fabric, the water solubility of fibers increases when exposed to liquid water or water vapor, causing the fabric to form a hydrogel and decrease gas permeability through the fabric. This tendency to solubilize is not acceptable for a fabric used in a facial mask where relatively unobstructed passage of air is required. Therefore, in one embodiment of the present invention, the method further comprises crosslinking the fibers of the fabric, before or after attaching the binding substance, by treating the fabric with one or more than one crosslinking agent that chemically bonds the fibers of the fabric to one another thereby preventing solubilization.

In one embodiment, treating the fabric with a crosslinking agent comprises contacting the fabric with an alkali, e.g., sodium hydroxide, to give the alkalinized cellulose in the case of cellulosic fabrics, and then reacting the fabric with the crosslinking agent. In one embodiment, the crosslinking agent is selected from the group consisting of dichloroalkanes, dimethylolureas, formaldehyde and trimethylolmelamines In a preferred embodiment, the crosslinking agent is an epoxy compound selected from the group consisting of diethylene glycol diglycidyl ether, ethylene glycol diglycidyl ether, epichlorohydrin, glycerin diglycidyl ether and vinylcyclohexene dioxide.

Adding one or more than one binding substance comprising a sulfate human pathogen binding group to the fibers can be accomplished, for example, by first, contacting the fabric with a suitable solvent, such as for example dimethylsulfoxide (DMSO) or dimethylformamide (DMF). The amount of time that the fabric is contacted with the solvent is adjusted to optimize fiber swelling, thereby increasing exposure of hydroxyl groups on the fiber surface to sulfation, as will be understood by those with skill in the art with reference to this disclosure.

Next, the solvent treated fabric is contacted with the binding substance, such as for example a sulfating reagent. Suitable sulfating reagents depend on the solvent used, as will be understood by those with skill in the art with reference to this disclosure. For example, in one embodiment, the solvent is dimethylsulfoxide, and the sulfating reagent is DMSO treated with sulfur trioxide ($DMSO-SO_3$). In another embodiment, the solvent is dimethylformamide, and the sulfating reagent is dimethylformamide treated with sulfur trioxide ($DMF-SO_3$). Contact with the binding substance is maintained until a satisfactory degree of covalent binding of the binding substance to the fibers is achieved but before excess binding substance binds to the fibers, which in the case of sulfate would render the fabric impermeable to gas upon contact with liquid water or water vapor, as will be understood by those with skill in the art with reference to this disclosure.

In one embodiment, the method further comprises rinsing the fabric with a solvent, such as for example ($DMSO-SO_3$) and ($DMF-SO_3$) and then contacting the fabric with a suitable base, such as for example sodium hydroxide, sodium acetate, or sodium bicarbonate, to neutralize an acidic binding substance such as an acidic sulfating agent, or to neutralize acid formed during the addition of the binding substance to the fabric.

The fabric is then washed with a suitable solvent, such as for example water or a simple alcohol (ethanol or isopropanol) to remove unreacted reagents yielding the sulfated fabric suitable for use in decreasing the transmission of one or more than one human pathogen, including viruses that cause human respiratory tract infections.

In another embodiment, the method of the present invention for making a fabric for use in decreasing the transmission of one or more than one human pathogen comprises, first, providing cellulose sulfate material made from cellulose pulp or cellulose powder and having a degree of sulfation greater than 0.2, and preferably greater than 0.5 sufficient to render the fibers water soluble. Next, the soluble cellulose sulfate is then applied to a fabric and covalently linked to the fibers of the fabric with a crosslinking agent, as disclosed above, as will be understood by those with skill in the art with reference to this disclosure. In this embodiment of the method, the fabric is not exposed to the relatively harsh sulfation conditions and reagents, but only to soluble cellulose sulfate and to the crosslinking reagents, and to the conditions for crosslinking, thereby reducing the potential for damage to the fabric that can occur if the sulfation reaction is not well controlled. A concentration of soluble cellulose sulfate is selected by testing, such that a fabric with acceptable pressure drop characteristics suitable for gas exchange through a facial mask is obtained, especially when the fabric is to be used in a mask according to the present invention, as will be understood by those with skill in the art with reference to this disclosure.

In one embodiment of the present invention, the method further comprises contacting the fabric with one or more than one substance that chemically disrupts a characteristic of the human pathogen essential for human pathogenicity. In a preferred embodiment, the one or more than one substance is a multivalent metallic ion, such as for example multivalent copper, multivalent silver or multivalent zinc, all of which are viricidal, bactericidal and fungicidal. In another embodiment, the one or more than one substance is a metallic salt, such as for example copper oxide, zinc acetate, copper acetate or copper sulfate, all of which are bactericidal, viricidal and fungicidal. In a preferred embodiment, the metallic salt is a divalent metallic salt. Acetate is advantageous as an anionic salt constituent as it is volatile and can be removed from the fabric by evaporation, but other anions are also suitable as salt components, including chlorides, oxides, iodides and others. The addition of the one or more than one substance to the fabric increases the effectiveness of the facial mask of the present invention in decreasing the transmission of one or more than one human pathogen by using mechanisms in addition to binding the human pathogen to the fabric.

In one embodiment of the present invention, the method further comprises incorporating one or more than one type of fiber other than the fibers comprising the binding substance, such as for example polyester fibers or polypropylene fibers, into the fabric.

In another embodiment, cellulosic fibers in the form of staple or tow are sulfated by the same types of sulfation reactions used for fabrics as disclosed in this disclosure, and then the cellulose sulfate fibers are washed and then formed into a nonwoven or woven fabric by conventional methods whereby cellulosic staple or tow are spun into threads or directly formed into nonwoven fabrics.

The method of the present invention for making a fabric for use in decreasing the transmission of one or more than one human pathogen, will now be disclosed with respect to the following examples.

EXAMPLE 1

Preparation of Sulfated Rayon Fabric

According to one embodiment of the present invention, sulfated rayon was prepared according to the present invention as follows. First, 60 ml isopropanol was chilled on ice and 0.2 grams $MgSO_4$ was added to the isopropanol to remove water. Next, 240 ml sulfuric acid, previously chilled on ice, was added to the isopropanol. Then, nonwoven rayon fabric having a density of 70 grams/meter$^2$ was cut into 17.5 cm by 22.5 cm rectangles and laid on polypropylene mesh of approximately the same size. Next, the rayon fabric on the mesh was submerged in chilled acetic acid for 15 minutes. Then, the isopropanol/sulfuric acid mixture was poured into a polyethylene box (approximately 30 cm by 37.5 cm) sitting on ice. Next, the rayon fabric on the polyethylene mesh was submerged in the isopropanol/sulfuric acid mixture for either 5 minutes or for 10 minutes, and rinsed first in cold isopropanol, and then in cold isopropanol containing 3 grams of sodium acetate per 100 ml, and then in cold isopropanol producing the sulfated rayon fabric. Next, the rayon fabric was then allowed to dry while still on the polyethylene mesh. Samples of the sulfated rayon fabric were analyzed for sulfur and carbon content. A 5 minute reaction time prior to rinsing was found to yield a degree of sulfation (DS) of approximately 0.1, while a 10 minute reaction time prior to rinsing was found to yield a degree of sulfation (DS) of approximately 0.2.

EXAMPLE 2

Preparation of Sulfonated Rayon Fabric

According to one embodiment of the present invention, sulfonated rayon fabric was prepared according to the present invention as follows. First, a solution was prepared by adding 30 grams of sodium sulfate to 600 grams distilled water, followed by adding of 4 grams of CI Reactive Blue 21 dye (a sulfonated binding substance). Next, 30 grams of nonwoven rayon fabric having a density of 70 grams/meter$^2$ were added to the solution and gently swirled until uniformly submerged and wetted. Then, 12 grams of sodium carbonate were added with stirring, and the mixture was held at 30° C. for 35 minutes. Next, the temperature was raised to 70° C. for an additional 60 minutes yielding the sulfonated rayon fabric (with CI Reactive Blue 21 dye as the binding substance). Then, the sulfonated rayon fabric was rinsed under running water until no more free dye was eluted, and the sulfonated rayon fabric was air-dried.

EXAMPLE 3

Preparation of Fabric Comprising One or More than One Substance that Destroys the Pathogenic Capacity of One or More than One Human Pathogen According to one embodiment of the present invention, sulfated cellulose fabric made according to Example 1 or sulfonated cellulose fabric made according to Example 2 was prepared to comprise one or more than one than one additional substance, other than the binding substance, that destroys the pathogenic capacity of one or more than one human pathogen as follows. First, sulfated rayon fabric was made according to the process disclosed in Example 1, or sulfonated rayon fabric (with CI Reactive Blue 21 dye as the binding substance) was made according to the process disclosed in Example 2. Then, copper sulfate and zinc acetate, both of which are divalent metal salts, were applied by aerosol to the fabric at 40 μl/cm$^2$ fabric using a concentration of 1 gram metal salt/100 milliliters of water. The fabric comprising the additional substance was then air-dried yielding sulfated rayon fabric comprising both divalent copper and divalent zinc ions, or sulfonated rayon fabric comprising both divalent copper and divalent zinc ions.

EXAMPLE 4

Industrial Process for Preparation of Sulfonated Rayon Fabric Comprising Divalent Metal Salts According to one embodiment of the present invention, sulfonated rayon fabric (with CI Reactive Blue 21 dye as the binding substance) and comprising divalent metal salts was prepared according to the present invention as follows. First, 100% spunlace viscose rayon fabric having a density of 70 grams/meter$^2$ was dyed with CI Reactive Blue 21 (Novacron® Turquoise H-GN) at a liquid to solid ratio of 20:1. Next, 50 g/L sodium sulfate, 20 g/L sodium carbonate and 12% dye by volume (120 ml/L) was added to a dye bath and mixed thoroughly with continuous agitation. Then, the rayon fabric was immersed in the dye bath for 35 minutes at a temperature of 30° C., followed by 60 minutes at a temperature of 70° C. producing the sulfonated rayon fabric (with CI Reactive Blue 21 dye as the binding substance). Next, the sulfonated rayon fabric was rinsed under running water and air-dried. Then, 50 grams each of copper acetate and zinc acetate per liter of water was sprayed on the sulfonated rayon at rate 0.08 L/m$^2$ producing the sulfonated rayon fabric comprising both divalent copper and divalent zinc ions. The sulfonated rayon fabric comprising both divalent copper and divalent zinc ions was again air-dried.

EXAMPLE 5

Assessment of Fabric for Anti-Human Pathogen Properties

Testing antiviral properties (as a surrogate for anti-human pathogen properties) of a fabric is performed by application of standardized amounts of a virus onto a piece of test fabric. The test fabric is then stirred in cell culture medium to elute any functional virus particles, that is, virus particles that are not inactivated by adherence to the fabric or otherwise to the test fabric. Functional virus particles eluted into the culture medium are assayed for viral activity by contacting the medium with cells susceptible to viral killing, and ascertaining a quantitative readout of cell death. Decreased cell death in the eluting medium indicates increased inactivation of the virus by the test fabric through viral adherence to the fabric or otherwise by the test fabric.

According to one embodiment of the present invention, sulfated rayon fabric having a degree of sulfation (DS) of 0.2, made according to Example 1, sulfonated rayon fabric (with CI Reactive Blue 21 dye as the binding substance), made according to Example 2, and sulfonated rayon fabric (with CI Reactive Blue 21 dye as the binding substance) comprising both copper sulfate and zinc acetate, made according to Example 3, were assessed for antiviral properties. First, test samples of the sulfated rayon fabric, the sulfonated rayon fabric (with CI Reactive Blue 21 dye as the binding substance), and the sulfonated rayon fabric (with CI Reactive Blue 21 dye as the binding substance) comprising both copper sulfate and zinc acetate were submitted to Microbiotest, Inc. (Sterling, Va. US) for assessment of the fabric's ability to inactivate the human pathogen herpes simplex virus (HSV). HSV was applied in an aerosol to a 5 cm by 5 cm area of the test fabrics, as well as to a non-sulfated, non-sulfonated piece of rayon control fabric, and to a piece of rayon fabric treated only with copper sulfate and zinc acetate (1 gram each per 100 ml water, applied at 40 microliters per square centimeter). The HSV-treated fabric samples were held for 1 minute and then placed in individual 20 ml aliquots of extraction medium and subjected to gentle agitation for 5 minutes. Aliquots of the extraction sample were serially diluted 10-fold in dilution medium and inoculated onto host cells. Residual infectious virus in extraction medium from each sample was detected and quantified by their viral-induced cytopathic effects.

TABLE 1

RESULTS OF ASSESSMENT OF FABRIC FOR ANTIVIRAL PROPERTIES

| FABRIC TESTED | LOGS OF INFECTIOUS HSV RECOVERED AFTER 1 MINUTE VIRUS CONTACT TIME WITH THE FABRIC |
|---|---|
| non-sulfated, non-sulfonated rayon control fabric | 7.60 ± 0.19 |
| non-sulfated, non-sulfonated rayon fabric treated with copper sulfate and zinc acetate | 5.60 ± 0.23 |
| sulfated rayon fabric | 5.73 ± 0.24 |
| sulfonated rayon fabric (with CI Reactive Blue 21 dye as the binding substance) | 7.23 |
| sulfonated rayon fabric (with CI Reactive Blue 21 dye as the binding substance) comprising copper sulfate and zinc acetate | undetectable (below 3.13) |

As can be seen, the sulfated rayon fabric prepared according to Example 1, had a 1.87 log reduction in pathogenic virus as compared to the non-sulfated, non-sulfonated rayon control fabric. Incorporating copper sulfate and zinc acetate to the non-sulfated, non-sulfonated rayon control fabric yielded a 2.0 log reduction in pathogenic virus as compared to the non-sulfated, non-sulfonated rayon control fabric, where the reduction in pathogenic virus was attributable to the presence of the divalent salts alone. Sulfonated rayon fabric (with CI Reactive Blue 21 dye as the binding substance) prepared according to Example 2 had a 0.37 log reduction in pathogenic virus as compared to the non-sulfated rayon control fabric.

The lower limit of detection in the assay system was 3.13 logs, so that the minimum reduction in HSV titer for sulfonated rayon fabric (with CI Reactive Blue 21 dye as the binding substance) and treated with copper sulfate and zinc acetate was 4.47 logs. Thus, a minimum of 2.47 logs further viral inactivation or trapping was achieved with sulfonation and divalent metal ions versus non-sulfated, non-sulfonated rayon fabric incorporating the same amount of divalent metal ions. These results demonstrate an unexpected synergy with respect to anti-human pathogen activity between sulfonation of a fabric and the incorporation of divalent metal salts into the fabric.

According to one embodiment of the present invention, sulfated rayon fabric having a degree of sulfation (DS) of either 0.1 or 0.2 made according to Example 1, sulfated rayon fabric having a degree of sulfation (DS) of 0.2 and comprising the divalent metal salts copper sulfate and zinc acetate made according to Example 4, sulfonated rayon fabric (with CI Reactive Blue 21 dye as the binding substance) made according to Example 2, and sulfonated rayon fabric (with CI Reactive Blue 21 dye as the binding substance) and comprising the divalent metal salts copper sulfate and zinc acetate made according to Example 3, as well as to a non-sulfated, non-sulfonated rayon control fabric, and rayon fabric comprising the divalent metal salts copper sulfate and zinc acetate were assessed for their antiviral properties. 4.70 logs of influenza A virus was applied in an aerosol to a 5 cm by 5 cm area of the test fabrics and three samples of each of the test fabrics with the applied influenza A virus were allowed to sit after virus application for either 1, 5, or 15 minutes, and then placed in individual 20 ml aliquots of extraction medium and subjected to gentle agitation for 5 minutes. Serial dilutions of extraction buffers were administered into embryonated eggs for assay of pathogenic influenza A viral titer by embryonic viability and by a hemaglutinin assay of allantoic fluid from such eggs.

The results of the testing were that the sulfated rayon fabric made according to Example 1 having a degree of sulfation (DS) of either 0.1 or 0.2, both yielded no detectable pathogenic virus at each of the time points tested (1, 5 and 15 minutes), indicating an influenza virus log reduction greater than 3 at each of the time points tested compared to the amount of virus applied to the fabric. Similarly, sulfated rayon fabric made according to Example 1 having a degree of sulfation (DS) of 0.2 and comprising the divalent metal salts copper sulfate and zinc acetate also yielded no detectable pathogenic virus at each of the time points tested (1, 5 and 15 minutes), indicating an influenza virus log reduction greater than 3 at each of the time points tested compared to the amount of virus applied to the fabric.

Sulfonated rayon fabric (with CI Reactive Blue 21 dye as the binding substance), made according to Example 2, reduced influenza A virus in log reductions of 1.95 at a 1 minute test time, 2.33 at a 5 minute test time, and 3.08 at 15 minute test time. Sulfonated rayon fabric (with CI Reactive Blue 21 dye as the binding substance) and comprising the divalent metal salts copper sulfate and zinc acetate made according to Example 3, yielded no detectable pathogenic virus at each of the time points tested (1, 5 and 15 minutes), indicating an influenza virus log reduction greater than 3 at each of the time points tested.

According to another embodiment of the present invention, there is provided a device for use in decreasing the transmission of one or more than one human pathogen, such as for example one or more than one virus that causes human respiratory tract infections. In one embodiment, the device comprises a fabric comprising one or more than one binding substance according to the present invention that binds one or more than one human pathogen, such as for example one or more than one type of virus that causes human respiratory tract infections. In a preferred embodiment, the device comprises a fabric according to the present invention. In one embodiment, the device is selected from the group consisting of an article of clothing, such as for example an absorbent tissue, an apron, a glove or a scarf, socks and shoe inserts; bed clothes, such as for example a sheet or a blanket; a cosmetic pad, a diaper, a dry sanitizing patch attached by an adhesive to any surface or any part of a body; a sanitary pad; a toilet cover, upholstery, such as for example a sofa covering; a wipe; and a window covering, such as for example a curtain or shade. In a preferred embodiment, the device is an air filter, such as is used in motor vehicles, such as for example airplanes and automobiles; or as used in non-mobile confined spaces, such as for example homes, hospitals and offices, where there is a risk of human pathogen transmission.

In a preferred embodiment, the device is a facial mask for decreasing the transmission of one or more than one human pathogen to and from a human wearer of the facial mask. The facial mask comprises a facepiece configured to cover the mouth and nose of the wearer of the facial mask, and comprising one or more than one extension for securing the facial mask to the head of the wearer.

In a preferred embodiment, the facepiece of the facial mask comprises a fabric according to the present invention, where the fabric comprises a binding substance according to the present invention. In a preferred embodiment, the fabric further comprises one or more than one additional substance according to the present invention, other than the binding substance, that decreases the pathogenic capacity of one or more than one human pathogen. In a preferred embodiment, the one or more than one additional substance is a multivalent metallic ion, such as for example a multivalent metallic ion selected from the group consisting of multivalent copper, multivalent silver and multivalent zinc. In another embodiment, the one or more than one substance is a metallic salt, such as for example a metallic salt selected from the group consisting of copper acetate, copper oxide, copper sulfate and zinc acetate. In a particularly preferred embodiment, the metallic salt is a divalent salt.

Figure 3:
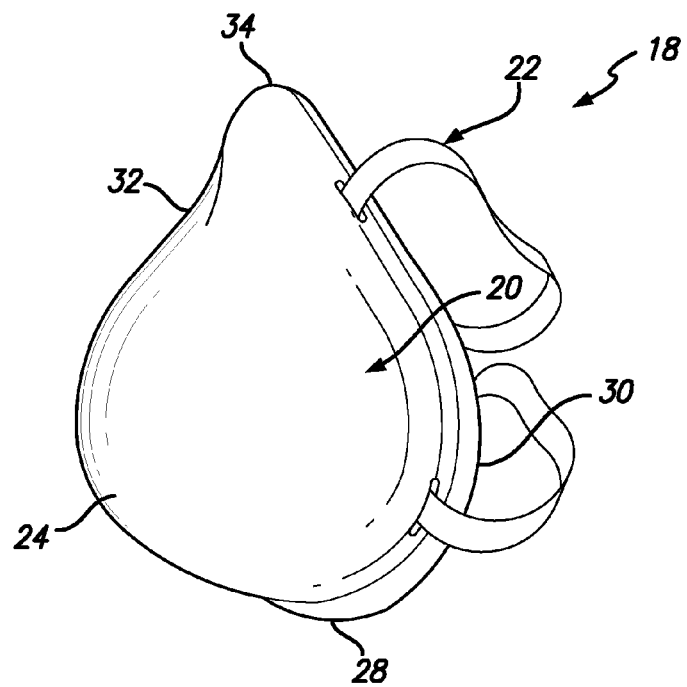
Figure 4:
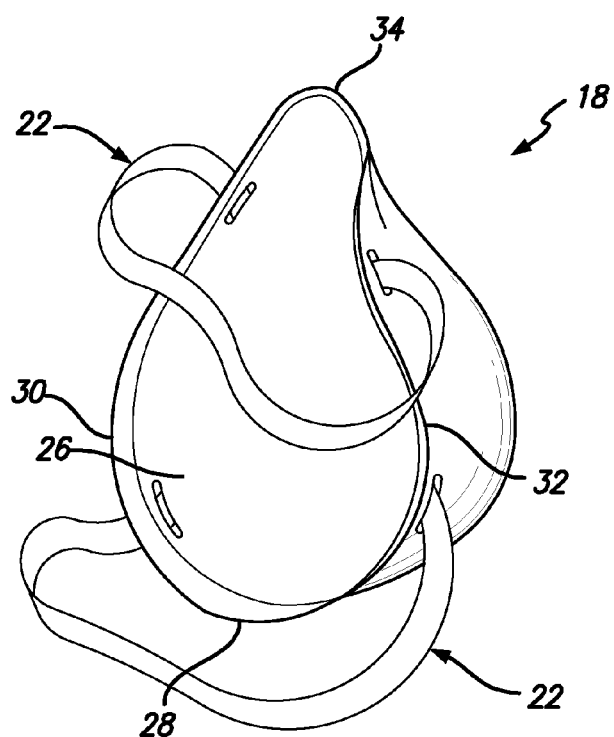
Figure 5:
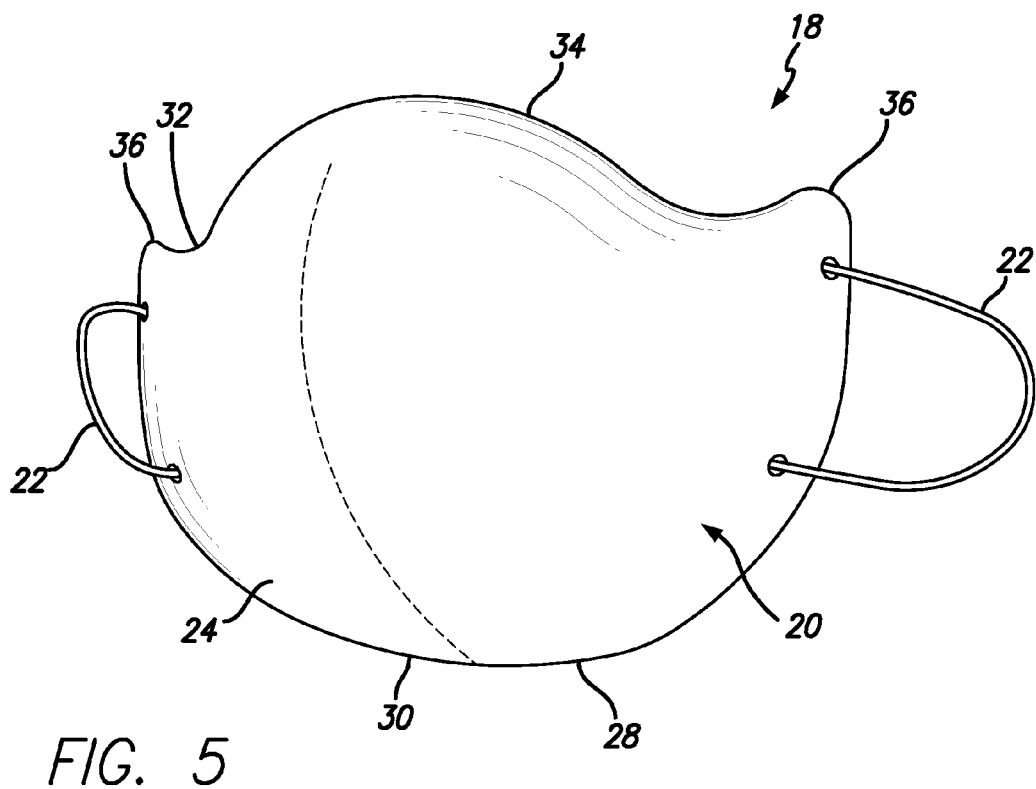
Figure 6:
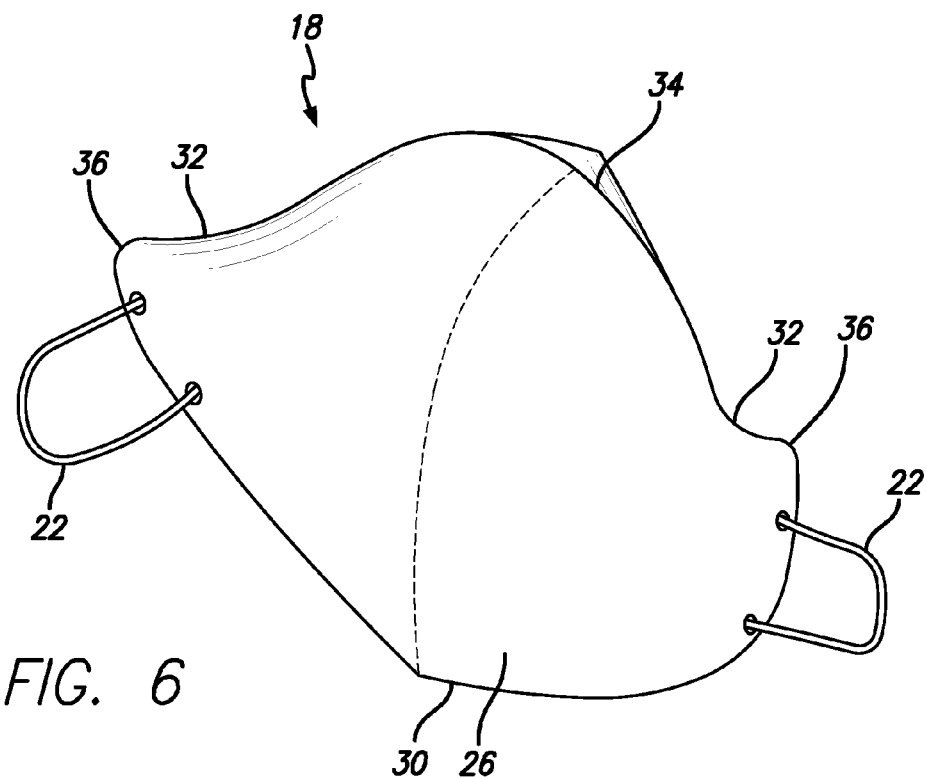
FIG. 6 is a back perspective view of the facial mask shown in FIG. 5.
Figure 7:
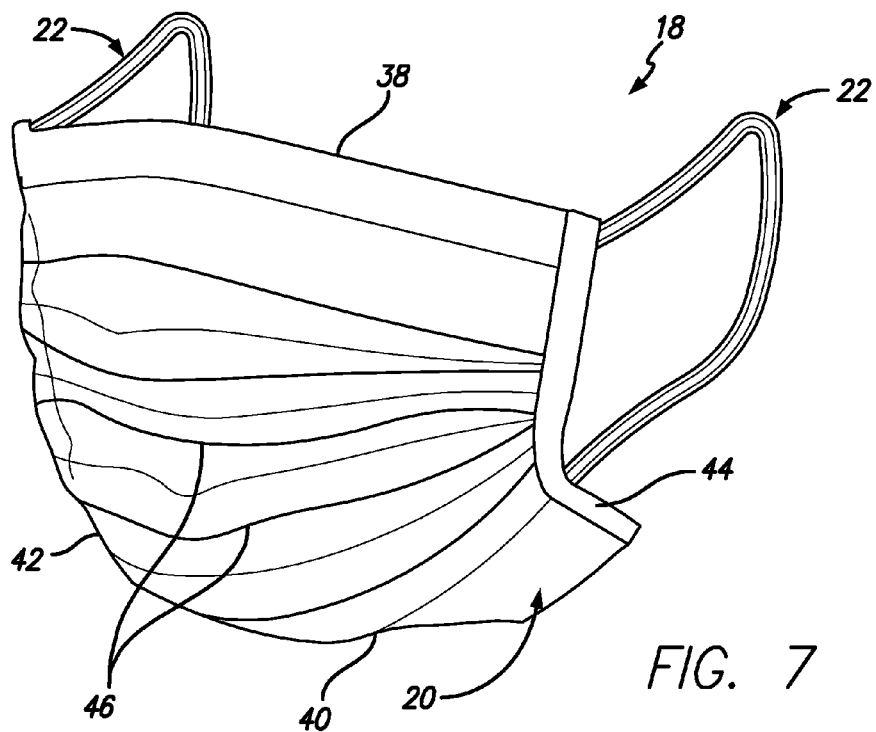
FIG. 7 is a front perspective view of a facial mask according to another embodiment of the present invention.
Figure 8:
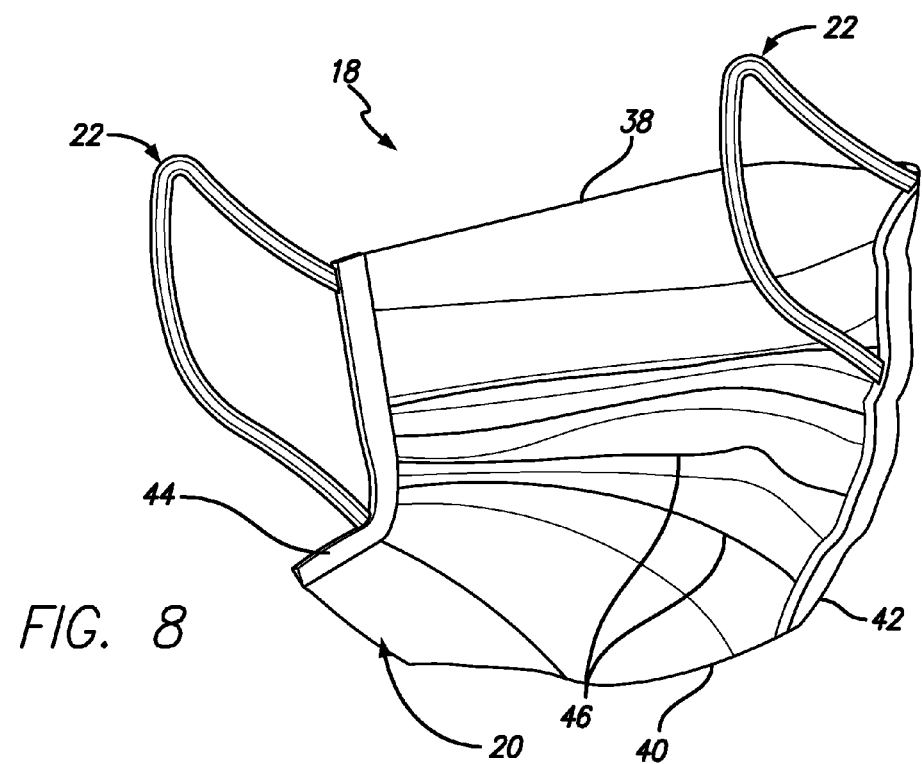
FIG. 8 is a back perspective view of the facial mask shown in FIG. 7.

Referring now to FIG. 3 through FIG. 8, there are shown, respectively, a front perspective view of a facial mask according to one embodiment of the present invention (FIG. 3); a back perspective view of the facial mask shown in FIG. 3 (FIG. 4); a front perspective view of a facial mask according to another embodiment of the present invention (FIG. 5); and a back perspective view of the facial mask shown in FIG. 5 (FIG. 6); a front perspective view of a facial mask according to another embodiment of the present invention (FIG. 7); and a back perspective view of the facial mask shown in FIG. 7 (FIG. 8). As can be seen, the facial mask 18 comprises a facepiece 20 and one or more than one extension 22 joined to the facepiece 20 for securing the facial mask 18 to the head of a wearer. The facepiece 20 comprises a front side 24, a back side 26 and a perimeter 28 around the front side 24 and back side 26, and the facepiece 20 is configured to cover the mouth and nose of the wearer of the facial mask 18 by comprising a form configured to fit the lower portion of the head of a wearer.

Referring now to FIG. 3 and FIG. 4, there are shown, respectively, a front perspective view of a facial mask according to one embodiment of the present invention (FIG. 3), and a back perspective view of the facial mask shown in FIG. 3 (FIG. 4). As can be seen, in this embodiment, when viewed from the front, the perimeter 28 of the facepiece 20 comprises a semi-circular lower half 30, and further comprises a semi-circular upper half 32 with a central nose bridge extension 34 configured to extend above the nostrils of the wearer, and onto the bridge of the nose of the wearer. In this embodiment of the facial mask 18, the facepiece 20 is molded to be convex toward the front side 24, in order to more closely approximate the facial curves of a wearer of the facial mask 18.

Referring now to FIG. 5 and FIG. 6, there are shown, respectively, a front perspective view of a facial mask according to another embodiment of the present invention (FIG. 5), and a back perspective view of the facial mask shown in FIG. 5 (FIG. 6). As can be seen, when viewed from the front, in this embodiment, the perimeter 28 of the facepiece 20 comprises a substantially semi-circular lower half 30, and comprises an upper half 32 with two cheek extensions 36 laterally, and a central nose bridge extension 34 between the two cheek extensions 36. As will be understood by those with skill in the art with reference to this disclosure, the cheek extensions 36 are configured to conform to the sides of the cheeks of the wearer of the facial mask 18, and the central nose bridge extension 34 is configured to extend above the nostrils of the wearer, and onto the bridge of the nose of the wearer. In this embodiment of the facial mask 18, the facepiece 20 is convex toward the front side 24 in order to more closely approximate the facial curves of a wearer of the facial mask 18.

Referring now to FIG. 7 and FIG. 8, there are shown, respectively, a front perspective view of a facial mask according to one embodiment of the present invention (FIG. 7), and a back perspective view of the facial mask shown in FIG. 7 (FIG. 8). As can be seen, in this embodiment, the perimeter 28 of the facepiece 20 comprises a top edge 38, a bottom edge 40, two lateral edges 42, 44 connecting the top edge 38 with the bottom edge 40. The facepiece 20 further comprises a plurality of pleats 46 extending from one lateral edge 42 to the other lateral edge 44, the pleats 46 allowing expansion of the facepiece 20 centrally thereby forming a convex shape toward the front side 24 of the facepiece 20 when expanded, in order to more closely approximate the facial curves of a wearer of the facial mask 18.

In one embodiment, the facepiece 20 comprises a fabric comprising a binding substance, according to the present invention. In a preferred embodiment, the facepiece comprises a fabric comprising a binding substance and one or more than one divalent metal ion. In a preferred embodiment, the facepiece comprises a material comprising a plurality of layers, according to the present invention. In a particularly preferred embodiment, the facepiece comprises a material, according to the present invention, comprising three layers, where one or more than one of the three layers is a fabric according to the present invention, and where one or more than one of the layers is a heat-moldable fabric, such as a heat-moldable fabric selected from the group consisting of polypropylene, polyester or non-woven cellulose acetate fabric. In a preferred embodiment, the heat-moldable fabric comprises polypropylene webbing.

The facial mask 18 further comprises one or more than one extension 22 joined to the facepiece 20 for securing the facial mask 18 to the head of a wearer. In one embodiment, the one or more than one extension 22 is a strap as seen in FIG. 3, or an ear loop as seen in FIG. 5 and FIG. 7. The strap can be elastic or non-elastic. In one embodiment, the one or more than one extension 22 is a series of adhesive strips to allow attachment of the facial mask 18 to the wearer's face.

Figure 9:
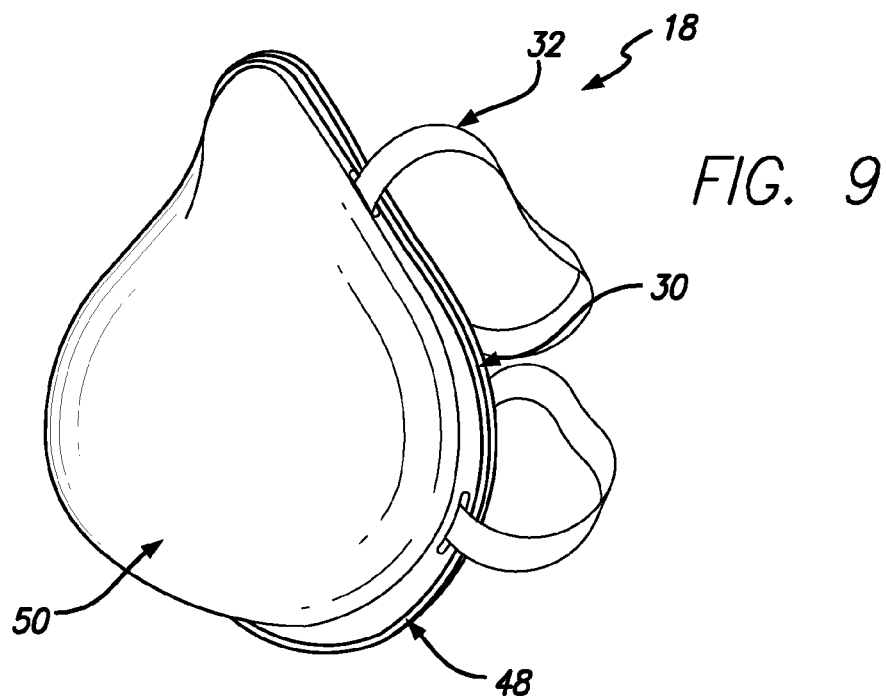
FIG. 9 and FIG. 10 are two front perspective views of two embodiments of facial masks comprising a removable filter according to the present invention.
Figure 10:
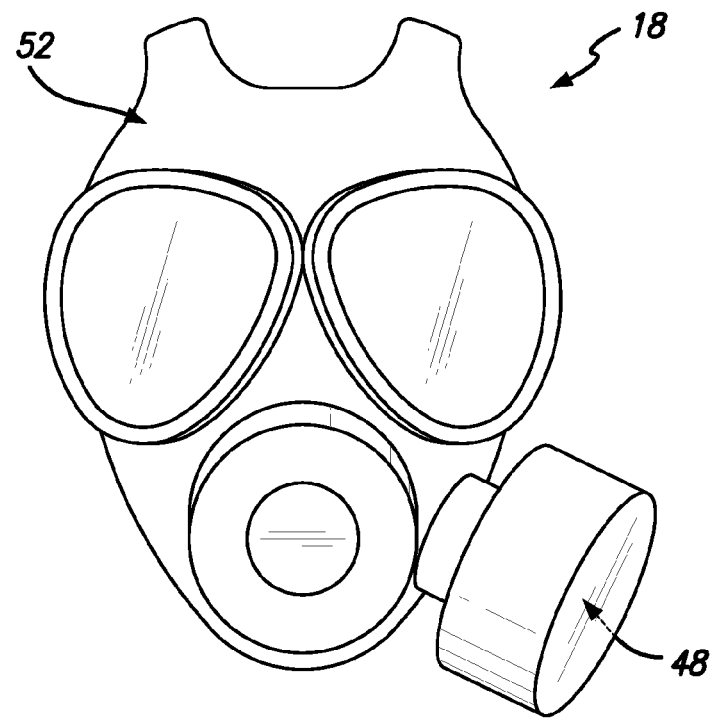

In another preferred embodiment, the device is a facial mask comprising a removable and replaceable filter comprising a fabric according to the present invention. Referring now to FIG. 9 and FIG. 10, there are front perspective views of two embodiments of facial masks comprising a removable filter according to the present invention. As can be seen, in one embodiment as shown in FIG. 9, the facial mask 18 comprises a facepiece 20 and a plurality of extensions 22, and further comprises a mechanism 48 for holding a filter, and a filter 50. In the embodiment shown in FIG. 9, the mechanism 48 is a two-part interconnecting frame allowing removable placement of the filter to be attached between the two parts of the frame of the facial mask 18. In another embodiment, as shown in FIG. 10, the facial mask 18 comprises a gas mask 52 and a plurality of extensions 22, and further comprises a mechanism 48 for holding a filter, and a filter 50. In a preferred embodiment, the filter comprises a fabric according to the present invention. In another preferred embodiment, the filter comprises a material according to the present invention, comprising a plurality of layers.

According to another embodiment of the present invention, there is provided a method for making a device for use in decreasing the transmission of one or more than one human pathogen, including viruses that cause human respiratory tract infections. In one embodiment, the method produces a device according to the present invention. In another embodiment, the method produces a device selected from the group consisting of an article of clothing, such as for example an absorbent tissue, an apron, a glove or a scarf, socks and shoe inserts; bed clothes, such as for example a sheet or a blanket; a cosmetic pad, a diaper, a dry sanitizing patch attached by an adhesive to any surface or any part of a body; a sanitary pad; a toilet cover, upholstery, such as for example a sofa covering; a wipe; and a window covering, such as for example a curtain or shade.

In a preferred embodiment, the device produced by the method is a facial mask for use in decreasing the transmission of one or more than one human pathogen to and from a human wearer of the facial mask, according to the present invention. The facial mask comprises a facepiece and one or more than one extension attached to the facepiece for securing the facial mask to the head of a wearer. In a preferred embodiment, the device produced by the method is a facial mask comprising a removable filter comprising a fabric according to the present invention. In another preferred embodiment, the device produced by the method is a covering for a facial mask or breathing apparatus, such as for example a layer of fabric that can be attached to an existing facial mask or breathing apparatus (such as for example a respiratory or gas mask), where the covering increases the safety of the wearer of the facial mask or breathing apparatus by decreasing the transmission of one or more than one human pathogen to and from a human wearer of the facial mask or breathing apparatus, as the wearer is breathing through the covering.

In another preferred embodiment, the device produced by the method is an air filter, such as is used in motor vehicles, such as for example airplanes and automobiles; or as used in non-mobile confined spaces, such as for example homes, hospitals and offices, where there is a risk of human pathogen transmission. The method comprises providing a fabric made according to the present invention, and incorporating the fabric into the device.

In one embodiment, the method comprises enclosing or surrounding the fabric comprising the binding substance with one or more than one heat-moldable fabric. Such heat-moldable fabrics permit shaping of masks with heat or ultrasonic welding of the facial mask In one embodiment, the method comprises, first, providing a fabric according to the present invention, where the fabric comprises a binding substance according to the present invention. In a preferred embodiment, the fabric further comprises one or more than one additional substance according to the present invention, other than the binding substance, that decreases the pathogenic capacity of one or more than one human pathogen. In a preferred embodiment, the one or more than one additional substance is a multivalent metallic ion, such as for example multivalent copper, multivalent silver or multivalent zinc. In another embodiment, the one or more than one substance is a metallic salt, such as for example copper oxide, zinc acetate, copper acetate or copper sulfate. In a particularly preferred embodiment, the metallic salt is a divalent metallic salt.

In one embodiment, the fabric is cut and formed to the shape of the facial mask, and the one or more than one extension is attached to the facial mask.

In another embodiment, the facepiece of the facial mask comprises a plurality of layers, where one or more than one of the layers comprises a fabric according to the present invention, comprising a binding substance, and where one or more than one of the layers is a heat-moldable fabric, such as for example polypropylene, polyester or cellulose acetate nonwoven fabric. In a particularly preferred embodiment, the plurality of layers is three layers. In another particularly preferred embodiment, the plurality of layers is four layers. When the facepiece comprises a plurality of layers, the method comprises providing fabric to form one or more than one layer of the facepiece of the facial mask. In one embodiment, the fabric or the material or both the fabric and the material are provided on rolls of a first size, and the rolls are cut to a suitable size for making the facial mask.

Then, the fabric and the one or more than one layer material are assembled in the order of the layers of the facepiece, and joined together. In one embodiment, the fabric and one or more than one layer of material are joined by ultrasonic welding. In a preferred embodiment, the fabric and one or more than one layer of material are joined by ultrasonic welding and by the application of pressure. In one embodiment, the facial mask has a perimeter and the fabric and one or more than one layer of material are joined by ultrasonic welding along the perimeter. In one embodiment, the method further comprises labeling the facial mask with text or graphics or both text and graphics.

Next, the method comprises shaping the facepiece. In one embodiment, shaping the facepiece comprises cutting the fabric, and the one or more than one layer of material if present, into the shape of the facepiece.

In one embodiment, the method further comprises joining two or more than two seams in the facepiece to change the three-dimensional structure of the facepiece. In one embodiment, joining comprises welding the facepiece or applying an adhesive to the facepiece.

Then, the method comprises attaching one or more than one extension to the facepiece to create the facial mask.

According to another embodiment of the present invention, there is provided a method of decreasing the transmission of one or more than one human pathogen. In one embodiment, the method comprises providing a facial mask according to the present invention, and wearing the facial mask.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A facial mask for use in decreasing the transmission of one or more than one human pathogen to and from a human wearer of the facial mask, the facial mask comprising:
   a) a facepiece comprising a front side, a back side and a perimeter around the front side and back side, and the facepiece is configured to cover the mouth and nose of the wearer of the facial mask; and
   b) one or more than one extension attached to the facepiece for securing the facial mask to the head of the wearer;
   where the facepiece comprises a material comprising three or more than three layers;
   where one or more than one of the three or more than three layers comprises a fabric having a hydroxyl group or an amino group, the fabric comprising one or more than one binding substance covalently bound to the fabric;
   where the one or more than one binding substance comprises one or more than one human pathogen binding group that chemically attaches the human pathogen to the binding substance;
   where the human pathogen binding group is covalently bound to the hydroxyl group or the amino group of the fabric, and the human pathogen binding group is selected from the group consisting of a sulfate group and a sulfonate group;
   where the fabric further comprises one or more than one type of multivalent metallic ion or metallic salt;
   where one or more than one of the three or more than three layers comprises a heat-moldable fabric; and
   where the fabric has a degree of sulfation or sulfonation between 0.02 and 2.

2. The facial mask of claim 1, where the facepiece comprises a substantially semi-circular lower half, and comprises an upper half with cheek extensions laterally, and a central nose bridge extension between the two cheek extensions configured to extend above the nostrils of the wearer, and onto the bridge of the nose of the wearer.

3. The facial mask of claim 1, where the binding substance is one or more than one reactive dye.

4. The facial mask of claim 3, where the reactive dye is selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86.

5. The facial mask of claim 1, where the multivalent metallic ion is selected from the group consisting of multivalent copper, multivalent silver and multivalent zinc; or where the metallic salt is selected from the group consisting of copper acetate, copper oxide, copper sulfate, and zinc acetate.

6. The facial mask of claim 1, where the human pathogen binding group selected from the group consisting of a sulfate group and a sulfonate group is human pathogen binding group consisting of a sulfated monosaccharide, a sulfated oligosaccharide, a sulfonated monosaccharide and a sulfonated oligosaccharide;
where the fabric comprises free hydroxyl groups or free amino groups;
and where the human pathogen binding group is linked to the free hydroxyl groups or the free amino groups of the fabric;
whereby the sulfate and sulfonate groups mimic the binding action of sialic acid groups on viruses.

7. The facial mask of claim 1, where the fabric has a degree of sulfation or sulfonation between 0.09 and 0.21.

8. A facial mask for use in decreasing the transmission of one or more than one human pathogen to and from a human wearer of the facial mask, the facial mask comprising:
a) a facepiece comprising a front side, a back side and a perimeter around the front side and back side, and the facepiece is configured to cover the mouth and nose of the wearer of the facial mask; and
b) one or more than one extension attached to the facepiece for securing the facial mask to the head of the wearer;
where the facepiece comprises a fabric having a hydroxyl group or an amino group, the fabric comprising one or more than one binding substance comprising one or more than one human pathogen binding group that chemically attaches the human pathogen to the binding substance covalently bound to the fabric;
where the human pathogen binding group is covalently bound to the hydroxyl group or the amino group of the fabric, and the human pathogen binding group is selected from the group consisting of a sulfate group and a sulfonate group;
where the fabric comprises one or more than one type of multivalent metallic ion or metallic salt; and
where the fabric has a degree of sulfation or sulfonation between 0.02 and 2.

9. The facial mask of claim 8, where the one or more than one human pathogen is selected from the group consisting of bacteria, fungi and viruses that cause human diseases.

10. The facial mask of claim 8, where the human pathogen is one or more than one virus that causes human respiratory tract infections.

11. The facial mask of claim 8, where the one or more than one human pathogen is selected from the group consisting of adeno-associated virus (AAV), herpes simplex virus (HSV), human papillomavirus (HPV), influenza viruses, rabies virus and respiratory syncytial virus (RSV).

12. The facial mask of claim 8, where the binding substance is one or more than one reactive dye.

13. The facial mask of claim 12, where the reactive dye is selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86.

14. The facial mask of claim 8, where the fabric further comprises one or more than one metallic salt selected from the group consisting of copper acetate, copper oxide, copper sulfate and zinc acetate.

15. The facial mask of claim 8, where the facepiece comprises a material comprising a plurality of layers; and where one or more than one of the plurality of layers comprises the fabric comprising the one or more than one binding substance.

16. The facial mask of claim 15, where one or more than one of the plurality of layers comprises a heat-moldable fabric.

17. The facial mask of claim 15, where one or more than one of the plurality of layers comprises a fabric selected from the group consisting of polypropylene, polyester or cellulose acetate nonwoven fabric.

18. The facial mask of claim 15, where one or more than one of the plurality of layers comprises polypropylene webbing.

19. The facial mask of claim 15, where the plurality of layers comprises three layers.

20. The facial mask of claim 15, where the plurality of layers comprises four layers.

21. A device for use in decreasing the transmission of one or more than one human pathogen, the device comprising a fabric having a hydroxyl group or an amino group, the fabric comprising one or more than one binding substance covalently bound to the fabric, the binding substance comprising one or more than one human pathogen binding group that chemically attaches the human pathogen to the binding substance;
where the device is selected from the group consisting of an air filter, an article of clothing, bed clothes, a cosmetic pad, a covering for a facial mask or breathing apparatus, a diaper, a dry sanitizing patch, a sanitary pad, a toilet cover, upholstery, a wipe, and a window covering; and
where the binding substance comprises a human pathogen binding group covalently bound to the hydroxyl group or the amino group, and the human pathogen binding group is selected from the group consisting of a sulfate group and a sulfonate group; and
where the fabric further comprises one or more than one type of multivalent metallic ion or metallic salt; and
where the fabric has a degree of sulfation or sulfonation between 0.02 and 2.

22. The device of claim 21, where the binding substance is one or more than one reactive dye.

23. The device of claim 22, where the reactive dye is selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86.

24. The device of claim 21, where the one or more than one type of multivalent metallic ion is selected from the group consisting of multivalent copper, multivalent silver and multivalent zinc.

25. The device of claim 21, where the one or more than one metallic salt is selected from the group consisting of copper acetate, copper oxide, copper sulfate and zinc acetate.

26. The device of claim 21, further comprising a material comprising a plurality of layers; and where one or more than one of the plurality of layers comprises the fabric comprising the one or more than one binding substance.

27. The device of claim 26, where one or more than one of the plurality of layers comprises a heat-moldable fabric.

28. The device of claim 26, where one or more than one of the plurality of layers comprises a fabric selected from the group consisting of polypropylene, polyester or cellulose acetate nonwoven fabric.

29. The device of claim 26, where one or more than one of the plurality of layers comprises polypropylene webbing.

30. The device of claim 26, where the plurality of layers comprises three layers.

31. The device of claim 26, where the plurality of layers comprises four layers.

32. A material for use in decreasing the transmission of one or more than one human pathogen, the material comprising a plurality of layers;
where one or more than one of the plurality of layers comprises a fabric having a hydroxyl group or an amino group, the fabric comprising the one or more than one binding substance covalently bound to the fabric:
where the binding substance comprises a human pathogen binding group covalently bound to the hydroxyl group or the amino group, and the human pathogen binding group is selected from the group consisting of a sulfate group and a sulfonate group that chemically binds the one or more than one human pathogen to the one or more than one binding substance; and
where the fabric further comprises one or more than one type of multivalent metallic ion or metallic salt; and
where the fabric has a degree of sulfation or sulfonation between 0.02 and 2.

33. The material of claim 32, where the binding substance is one or more than one reactive dye.

34. The material of claim 32, where the reactive dye is selected from the
group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86.

35. The material of claim 32, where the one or more than one type of multivalent metallic ion is selected from the group consisting of multivalent copper, multivalent silver and multivalent zinc.

36. The material of claim 32, where the one or more than one metallic salt is selected from the group consisting of copper acetate, copper oxide, copper sulfate and zinc acetate.

37. The material of claim 32, where one or more than one of the plurality of layers comprises a heat-moldable fabric.

38. The material of claim 32, where one or more than one of the plurality of layers comprises a fabric selected from the group consisting of polypropylene, polyester or cellulose acetate nonwoven fabric.

39. The material of claim 32, where one or more than one of the plurality of layers comprises polypropylene webbing.

40. The material of claim 32, where the plurality of layers comprises three layers.

41. The material of claim 32, where the plurality of layers comprises four layers.

42. A facial mask for use in decreasing the transmission of one or more than one human pathogen to and from a human wearer of the facial mask, the facial mask comprising:
a) a facepiece comprising a front side, a back side and a perimeter around the front side and back side, and the facepiece is configured to cover the mouth and nose of the wearer of the facial mask; and
b) one or more than one extension attached to the facepiece for securing the facial mask to the head of the wearer;
where the facepiece comprises a material comprising three or more than three layers;
where one or more than one of the three or more than three layers comprises a fabric comprising one or more than one binding substance;
where the one or more than one binding substance is one or more than one reactive dye comprising a linker group covalently bound to the fabric;
where the one or more than one binding substance comprises one or more than one human pathogen binding group that chemically attaches the human pathogen to the binding substance chemically bound to the reactive dye;
where the human pathogen binding group is selected from the group consisting of a sulfate group and a sulfonate group;
where the fabric further comprises one or more than one type of multivalent metallic ion or metallic salt; and,
where one or more than one of the three or more than three layers comprises a heat-moldable fabric;
whereby the reactive dye prevents the human pathogen binding group from forming a hydrogel in the fabric, thereby allowing gas permeability through the fabric;
whereby the reactive dye covalently bound to the fabric increases immobilization of human pathogens compared to the amount of immobilization of human pathogens on a fabric not having the reactive dye covalently bound to the fabric; and
where the fabric has a degree of sulfation or sulfonation between 0.02 and 2.

43. The facial mask of claim 42, where the reactive dye is selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86.

44. The facial mask of claim 43, where the multivalent metallic ion is selected from the group consisting of multivalent copper, multivalent silver and multivalent zinc; or where the metallic salt is selected from the group consisting of copper acetate, copper oxide, copper sulfate, and zinc acetate.

* * * * *